US012806146B2

(12) United States Patent
Yoshihara et al.

(10) Patent No.: US 12,806,146 B2
(45) Date of Patent: Nov. 24, 2026

(54) GRANULES INCLUDING STEARIC ACID AS A MELT COMPONENT, AND AMINOALKYL METHACRYLATE COPOLYMER E AS A POLYMER, AND PREPARATION USING SAME

(71) Applicant: SAWAI PHARMACEUTICAL Co., Ltd., Osaka City (JP)

(72) Inventors: Naoki Yoshihara, Osaka City (JP); Shota Hashimoto, Osaka City (JP); Ryota Kimata, Osaka City (JP)

(73) Assignee: SAWAI PHARMACEUTICAL CO., LTD., Osaka City (JP)

(*) Notice: Subject to any disclaimer, the term of this patent is extended or adjusted under 35 U.S.C. 154(b) by 949 days.

(21) Appl. No.: 17/942,333

(22) Filed: Sep. 12, 2022

(65) Prior Publication Data

US 2023/0014578 A1 Jan. 19, 2023

Related U.S. Application Data

(63) Continuation of application No. PCT/JP2021/009284, filed on Mar. 9, 2021.

(60) Provisional application No. 62/988,083, filed on Mar. 11, 2020.

(51) Int. Cl.

| | |
|---|---|
| ***A61K 31/4985*** | (2006.01) |
| ***A61K 9/16*** | (2006.01) |
| ***C07D 487/04*** | (2006.01) |

(52) U.S. Cl.

CPC .......... *A61K 9/1635* (2013.01); *A61K 9/1617* (2013.01); *A61K 9/1652* (2013.01); *A61K 31/4985* (2013.01)

(58) Field of Classification Search

CPC .......................... A61K 31/4985; C07D 487/04

USPC .......................................... 514/249; 544/350

See application file for complete search history.

(56) References Cited

U.S. PATENT DOCUMENTS

| | | | |
|---|---|---|---|
| 5,707,646 | A | 1/1998 | Yajima et al. |
| 2004/0175422 | A1 | 9/2004 | Tomohira |
| 2005/0106245 | A1 | 5/2005 | Yuso |
| 2008/0031965 | A1 | 2/2008 | Ikuta et al. |
| 2015/0313885 | A1 | 11/2015 | Merillon et al. |
| 2020/0009060 | A1 | 1/2020 | Miller et al. |

FOREIGN PATENT DOCUMENTS

| | | | |
|---|---|---|---|
| CN | 1509185 | A | 6/2004 |
| CN | 1638742 | A | 7/2005 |
| CN | 1960716 | A | 5/2007 |
| EP | 2 283 816 | A1 | 2/2011 |
| JP | H5-194193 | A | 8/1993 |
| JP | H6-116138 | A | 4/1994 |
| JP | 2015-54822 | A | 3/2015 |
| JP | 2016-511223 | A | 4/2016 |
| JP | 2018-83809 | A | 5/2018 |
| JP | 2018-154596 | A | 10/2018 |
| JP | 2019-514993 | A | 6/2019 |
| WO | 02/45693 | A1 | 6/2002 |
| WO | 2011/124953 | A2 | 10/2011 |
| WO | 2017/196712 | A1 | 11/2017 |

OTHER PUBLICATIONS

Office Action issued on Jan. 16, 2025 for corresponding Korean Patent Application No. 10-2022-7026916, along with an English translation (14 pages).

Office Action issued on Apr. 23, 2024 for corresponding Japanese Patent Application No. 2022-507218, along with an English machine translation (6 pages).

Final Office Action dated May 22, 2024 for corresponding Chinese Patent Application No. 202180017989.5, along with an English machine translation (12 pages).

Feng Yi, "Theory and practice of solid preparation technology of traditional Chinese medicine", China Press of Traditional Chinese Medicine, Mar. 2017, ISBN 978-7-5132-2464-2, pp. 194-195, along with an English machine translation.

Office Action issued on Apr. 29, 2023 for corresponding Chinese Patent Application No. 202180017989.5, along with an English machine translation (9 pages).

National Pharmacopoeia Commission ed., "Handbook of Comparison of Standards for Pharmaceutical Excipients in Countries", China Medical Science and Technology Press, 2016, pp. 272-273, along with an English translation (6 pages), cited in NPL No. 1.

Fang, Liang et al., "Pharmaceutical Polymer Material Science", China Medical Science and Technology Press, 2015, p.149, along with an English translation (4 pages), cited in NPL No. 1.

Office Action issued on Nov. 28, 2023 for corresponding Japanese Patent Application No. 2022-507218, along with an English machine translation (7 pages).

Office Action issued on Dec. 1, 2023 for corresponding Chinese Patent Application No. 202180017989.5, along with an English machine translation (11 pages).

Office Action issued on Aug. 8, 2023, for corresponding Japanese Patent Application No. 2022-507218, along with an English translation (11 pages).

(Continued)

*Primary Examiner* — Douglas M Willis

(74) *Attorney, Agent, or Firm* — HAUPTMAN HAM, LLP

(57) ABSTRACT

Provided is a melt granulated product with a high particle size homogeneity. Also, provided is a pharmaceutical composition using said melt granulated product. Also, provided is a melt granulated product with a high drug content. Also, provided is a pharmaceutical composition using the melt granulated product. According to one embodiment of the present invention, a granule is provided that comprises an active ingredient, stearic acid as a melt component, and aminoalkyl methacrylate copolymer E as a polymer, wherein the active ingredient, the stearic acid and the aminoalkyl methacrylate copolymer E are bound. In addition, the melt component may be solid at room temperature, and have a melting point of 100 °C or less. The polymer may be solid at room temperature, and have a glass transition point of 100 °C or less.

6 Claims, 3 Drawing Sheets

(56) References Cited

OTHER PUBLICATIONS

Communication pursuant to Article 94(3) EPC dated Apr. 22, 2025 for corresponding European Patent Application No. 21766854.0 (5 pages).

International Search Report issued for corresponding International Patent Application No. PCT/JP2021/009284 on Apr. 27, 2021, along with an English translation (5 pages).

Written Opinion issued for corresponding International Patent Application No. PCT/JP2021/009284 on Apr. 27, 2021 (4 pages).

Pawar et al., "Development and Evaluation of Taste Masked Granular Formulation of Satranidazole by Melt Granulation Technique", Journal of Pharmaceutics, 2014, vol. 2014, Article ID 789676, pp. 1-7 (7 pages), cited in NPL Nos. 1 and 2.

Office Action issued for corresponding Taiwanese Patent Application No. 110108516 on Jan. 6, 2022, along with an English translation (8 pages).

Kelleher et al., "Metformin Hydrochloride and Sitagliptin Phosphate Fixed Dose Combination Product Prepared Using Melt Granulation Continuous Processing Technology", AAPS PharmSciTech, vol. 21, Article No. 23 (2020), Published: Dec. 12, 2019 (44 pages), cited in NPL No. 4.

The Extended European Search Report issued on Jan. 3, 2024 for corresponding European Patent Application No. 21766854.0 (10 pages).

Office Action dated Aug. 12, 2025 for corresponding Korean Patent Application No. 10-2022-7026916; with English machine translation (19 pages).

English translation of Written Opinion of the International Searching Authority issued on Apr. 27, 2021 for corresponding International Patent Application No. PCT/JP2021/009284 (4 pages).

Communication pursuant to Article 94(3) EPC issued on Apr. 28, 2026 for corresponding European Patent Application No. 21 766 854.0 (6 pages).

GRANULES INCLUDING STEARIC ACID AS A MELT COMPONENT, AND AMINOALKYL METHACRYLATE COPOLYMER E AS A POLYMER, AND PREPARATION USING SAME

CROSS-REFERENCE TO RELATED APPLICATIONS

This application is a Continuation of International Patent Application No. PCT/JP2021/009284, filed on Mar. 9, 2021, which claims the benefit of priority to the U.S. Provisional Application No. 62/988,083, filed on Mar. 11, 2020, the entire contents of which are incorporated herein by reference.

FIELD

The present invention relates to granules containing an active ingredient at a high content and having a uniform particle size, and a preparation using the same.

BACKGROUND

In order to improve the manufacturability of a pharmaceutical preparation, the active ingredient is granulated with various additive agents. The granulation method is divided into wet granulation and dry granulation depending on the presence or absence of a solvent. When granulating an active ingredient which is unstable in water, a dry granulation method which does not use a solvent is selected. Among the dry granulation methods, the melt granulation method in which an additive agent is melted by heat and used as a binder is known.

On the other hand, since the melt granulation method is greatly affected by the physical properties of the melt component, it is difficult to control the particle size of the granulated product. In addition, since the melt granulation method uses a melt component instead of a solvent, it is difficult to increase the content of the active ingredient in the granulated product, and as a result, the problem that the formulation inevitably becomes large and the medication adherence decreases arises. For example, Japanese laid-open patent publication No. 2016-511223 describes drug-containing particles produced by the melt granulation method. However, the particles described in Japanese laid-open patent publication No. 2016-511223 have not been studied at all for the control of granulated particles.

SUMMARY

One object of the present invention is to provide a melt granulated product having a uniform particle size. Another object of the present invention is to provide a pharmaceutical composition using the melt granulated product.

Alternatively, one object of the present invention is to provide a melt granulated product having a high drug content. Another object of the present invention is to provide a pharmaceutical composition using the melt granulated product.

According to one embodiment of the present invention, a granule is provided that comprises an active ingredient, a melt component, and a polymer, wherein the active ingredient, the melt component, and the polymer are bound.

The melt component may be solid at room temperature and have a melting point of 100 °C or lower.

The polymer may be solid at room temperature and have a glass transition point of 100 °C or lower.

The polymer may be selected from a group consisting of aminoalkyl methacrylate copolymers, ammonioalkyl methacrylate copolymers, methacrylic acid copolymers, hypromellose acetate succinates, and polyvinylpyrrolidones, when the melt component is stearic acid or lauromacrogol.

The granule may have a structure in which the active ingredient, the melt component, and the polymer are mixed with each other by melting.

The granule may have a structure in which a part of the active ingredient, the melt component and the polymer are bound to each other by melting.

50% by mass or more of the active ingredient may be contained with respect to the total mass of the active ingredient, the melt component and the polymer.

According to one embodiment of the present invention, a preparation is provided that comprises any of the above granules and one or more pharmaceutically acceptable additive agents.

The additive may be a disintegrant.

DESCRIPTION OF EMBODIMENTS

Figure 1:
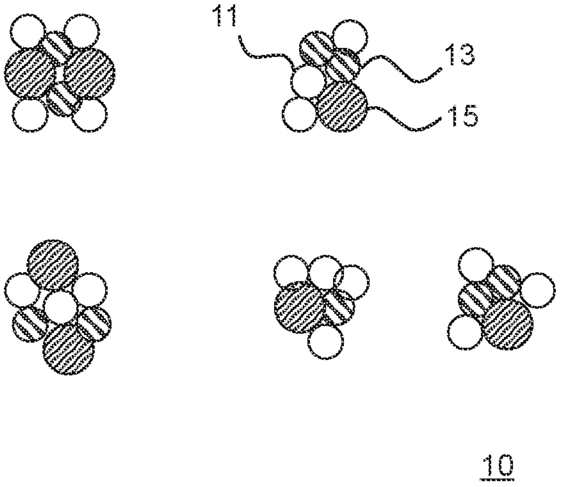
FIG. 1 is a schematic diagram which shows a granule according to one embodiment of the invention.

Hereinafter, a granule according to the present invention and the preparation using the same will be described with reference to drawings. In addition, the granule of the present invention and the preparation using the same are not construed as being limited to the description contents of the embodiments and examples shown below. In the drawings referred to in the present embodiment and the examples described later, the same parts or parts having the same functions are designated by the same reference numerals, and the repeated description thereof will be omitted.

FIG. 1 is a schematic diagram (cross-sectional view) showing a granule 10 according to one embodiment of the present invention. The granule 10 contains an active ingredient 11, a melt component 13, and a polymer 15. The granule 10 is a particle formed by binding the active ingredient 11, the melt component 13, and the polymer 15 by melt granulation. In the granule 10, the active ingredient 11 is not particularly limited. In the method for producing the granules 10, a solvent, particularly water, is not used, so that a water-unstable active ingredient can be preferably used.

The melt component 13 constituting the granule 10 is selected from oil-based additive agents applicable to melt granulation. In addition, the melt component 13 is preferably selected from additive agents in which the active ingredient 11 is not denatured and a significant increase in related substances is not observed by contact with the active ingredient 11. In order to form the granules 10 by the melt granulation method, the melt component 13 is selected from additive agents that are solid at room temperature. Considering the temperature range generally used in the melt granulation method, the melt component 13 is preferably selected from the additive agents having a melting point of 100 °C or lower, and preferably selected from additive agents having the melting point in a temperature range in which the active ingredient 11 is not denatured and a significant increase in related substances is not observed. Further, the melt component 13 is selected in consideration of the combination with the polymer 15.

The polymer 15 is selected from additive agents having compatibility with the melt component and are applicable to melt granulation. The expression that the polymer is "compatible" with respect to the melt component means that the melt component and the polymer are not separated from each other. Alternatively, it indicates a state in which the polymer is dispersed in the melt component, or a state in which the melt component is dispersed in the polymer. In one embodiment, the state in which the melt component and the polymer are not separated can be confirmed by an increase in the viscosity of the mixture (liquid or semi-solid having fluidity) when the melt component and the polymer are mixed and the melt component is melted. In addition, the polymer 15 is preferably selected from additive agents in which the active ingredient 11 is not denatured and a significant increase in related substances is not observed by contact with the active ingredient 11. In order to form the granules 10 by the melt granulation method, the polymer 15 is selected from additive agents that are solid at room temperature. Considering the temperature range generally used in the melt granulation method, the polymer 15 is preferably selected from additive agents having a glass transition point of 100 °C or lower, and preferably selected from additive agents having the glass transition point in a temperature range in which the active ingredient 11 is not denatured and a significant increase in related substances is not observed. Further, the polymer 15 is selected in consideration of the combination with the melt component 13.

As such a combination of the melt component 13 and the polymer 15, when the melt component 13 is stearic acid or lauromacrogol, an aminoalkyl methacrylate copolymer, an ammonioalkyl methacrylate copolymer, a methacrylic acid copolymer, a hypromellose acetate succinate or a polyvinylpyrrolidone as the polymer 15 can be combined. More preferably, stearic acid as the melt component 13 can be combined with the aminoalkyl methacrylate copolymer, the ammonioalkyl methacrylate copolymer, or the polyvinylpyrrolidone as the polymer 15. Alternatively, lauromacrogol as the melt component 13 can be combined with the aminoalkyl methacrylate copolymer, the ammonioalkyl methacrylate copolymer, the methacrylic acid copolymer, or the hypromellose acetate succinate as the polymer 15.

In the granule 10, the active ingredient 11, the melt component 13, and the polymer 15 need only form granules, and the active ingredient 11, the melt component 13, and the polymer 15 may have a structure in which the active ingredient 11, the melt component 13, and the polymer 15 are mixed with each other by melting, or may have a structure in which a part of the active ingredient 11, the melt component 13, and the polymer 15 are bound to each other by melting.

The granule 10 preferably contains the active ingredient 11 as the main component. The granule 10 preferably contains 50% by mass or more of the active ingredient 11 with respect to the total mass of the active ingredient 11, the melt component 13, and the polymer 15. In other words, it is preferable that the granule 10 contains a small amount of the melt component 13 and the polymer 15 within a formable range. Thereby, the content of the active ingredient 11 in the granule 10 can be effectively increased. Further, the granule 10 has a high uniformity of the particle size of the granulated product.

[Method for Producing Granules]

Figure 2:
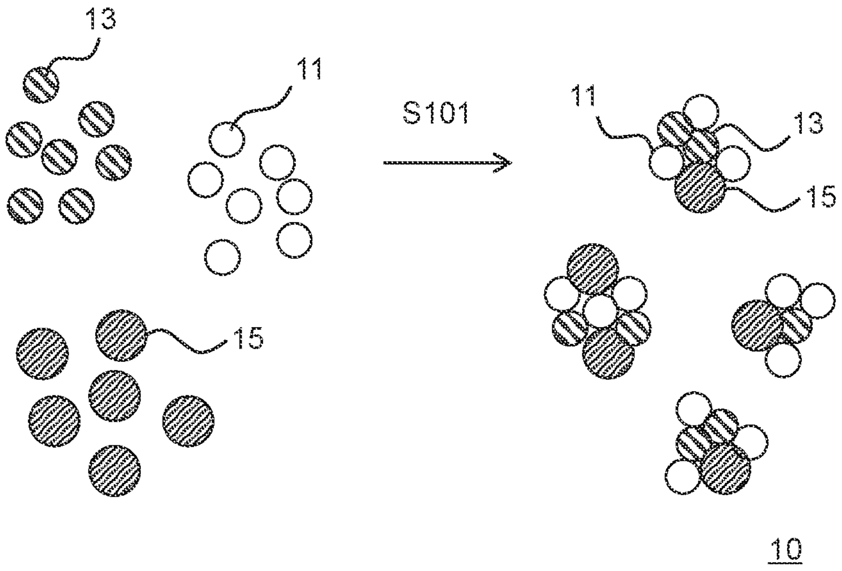
FIG. 2 is a flow diagram which illustrates a producing method of the granule according to one embodiment of the invention.

FIG. 2 is a flow diagram illustrating a method for producing granules according to one embodiment of the present invention. The active ingredient 11, the melt component 13 and the polymer 15 are mixed, and the active ingredient 11, the melt component 13 and the polymer 15 are melted and granulated by a melt granulation method to form granules 10 (S101). At this time, the temperature of these additive agents is heated to a temperature equal to or higher than the melting point of the melt component 13 and equal to or higher than the glass transition point of the polymer 15. Considering the temperature range generally used in the melt granulation method, the heating temperature is 100 °C or lower. It is preferable to perform the melt granulation in a temperature range in which the active ingredient 11 is not denatured and a significant increase in related substances is not observed.

By producing the granules 10 under such temperature control, the active ingredient 11, the melt component 13, and the polymer 15 can be bound to each other to produce the granules 10. As described above, the granules 10 can be easily produced by the melt granulation method.

[Preparation]

A pharmaceutical preparation using the granule 10 can be produced. For example, the granule 10 and a known pharmaceutically acceptable additive agent may be mixed to prepare a pharmaceutical composition. Alternatively, the pharmaceutical composition may be tableted into a tablet. In addition, the pharmaceutical composition to which the disintegrant is added may be tableted to obtain an orally disintegrating tablet. Further, the pharmaceutical composition may be encapsulated to form a capsule.

EXAMPLE

Test Example

After mixing 1 g of the melt component and 1 g of the polymer, the mixture was heated at 80 °C for 2 hours. In addition, 2 g of the melt component was also heated at 80 °C for 2 hours in the same manner, and the comparison of the viscosities of only the melt component and the melt component in which the polymer was mixed were evaluated by touch. Lauromacrogol (Nippon Surfactant Industry Co., Ltd.), stearic acid (NOF Corporation) or hardened oil (FREUND CORPORATION, Lubriwax) was used as the melt component. Aminoalkyl methacrylate copolymer E (Evonik, Eudragit (registered trademark) EPO), ammonioalkyl methacrylate copolymer RL (Evonik, Eudragit (registered trademark) RLPO), methacrylic acid copolymer L (Evonik, Eudragit (registered trademark) L100-55), hypromellose acetate succinate (Shin-Etsu Chemical Co., Ltd., Shin-Etsu AQOAT (registered trademark) HPMC AS LF), or polyvinylpyrrolidone (BASF, K30) was used as the polymer.

The evaluation results are shown in Table 1.

TABLE 1

| | | Melt components | | |
|---|---|---|---|---|
| | | Lauromacrogol | Stearic acid | Hardened oil |
| Polymers | Eudragit EPO | ○ | ◎ | X |
| | Eudragit RLPO | ○ | ○ | X |
| | Eudragit L100-55 | ◎ | — | X |

TABLE 1-continued

| | Melt components | | |
|---|---|---|---|
| | Lauromacrogol | Stearic acid | Hardened oil |
| HPMC AS LF | ○ | — | X |
| PVP (K30) | — | ◎ | X |

◎ viscosity significantly increased,
○ viscosity increased,
X No change
— not examined.

It was revealed that the aminoalkyl methacrylate copolymer, the ammonioalkyl methacrylate copolymer, the methacrylic acid copolymer, and the hypromellose acetate succinate increased in viscosity and showed compatibility when lauromacrogol was used as the melt component. In particular, it was revealed that the methacrylic acid copolymer showed excellent compatibility with lauromacrogol. Further, it was revealed that the aminoalkyl methacrylate copolymer, the ammonioalkyl methacrylate copolymer, and the polyvinylpyrrolidone increased in viscosity and the showed compatibility when stearic acid was used as the melt component. In particular, it was revealed that the aminoalkyl methacrylate copolymer and the polyvinylpyrrolidone showed excellent compatibility with stearic acid. On the other hand, none of the polymers showed compatibility when hydrogenated oil was used as the melt component.

Figure 3:
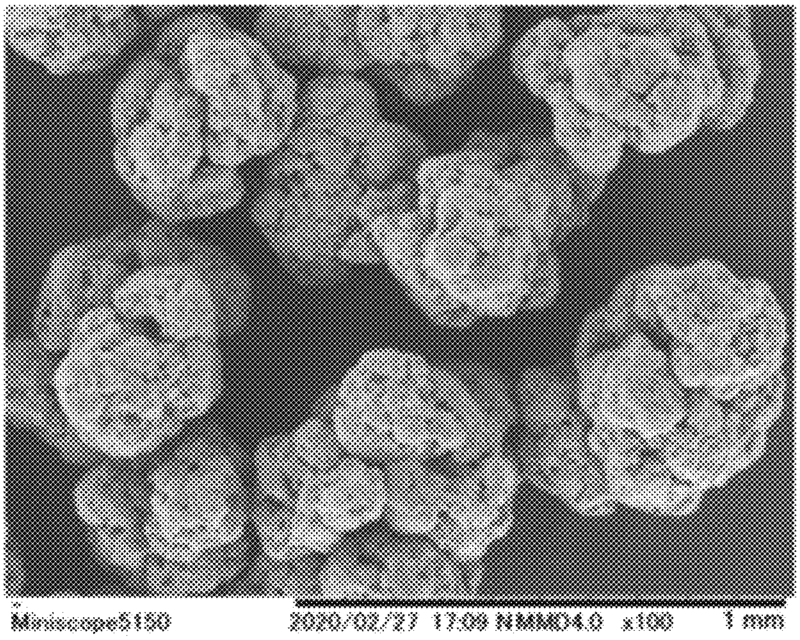
FIG. 3 is a scanning electron microscope (SEM) image of the granules of Example 1.

A scanning electron microscope (SEM) image of the obtained granules is shown in FIG. 3.

Comparative Example 1

310.2 g of sitagliptin phosphate as the active ingredient, 37.5 g of a hydrogenated oil (FREUND CORPORATION, Lubriwax) as the melt component, and 37.5 g of aminoalkyl methacrylate copolymer E (Evonik, Eudragit (registered trademark) EPO) as the polymer were put into a tumbling granulator (Powrex Corporation, MP-01), and granulation was performed at a rotor rotation speed of 400 rpm, an air supply air volume of 0.24 L/min to 0.37 L/min, and an air supply temperature of 82.9 °C to 89.6 °C for 100 minutes. At this time, the temperature of the additive agents was 55.4 °C to 68.1 °C. Since the compatibility between the hydrogenated oil and the aminoalkyl methacrylate copolymer E was not good, each component was not granulated and remained as a powder mixture even after the granulation step.

Additive amounts shown in Table 2 using sitagliptin phosphate as the active ingredient, stearic acid (NOF CORPORATION) as the melt component, and aminoalkyl methacrylate copolymer E (Evonik, Eudragit (registered trademark) EPO) as the polymer were put into a tumbling granulator (Powrex Corporation, MP-01) to produce granules under the respective production conditions. The particle size of the produced granules was measured using a laser diffraction/scattering method measuring device (Beckman Coulter Co., Ltd., LS 13 320).

TABLE 2

| | | Example 2 Ratio of active ingredient 80% | Example 3 Ratio of active ingredient 85% | Example 4 Ratio of active ingredient 90% | Example 5 Ratio of active ingredient 86% | Example 6 Ratio of active ingredient 86% | Comparative example 2 Ratio of active ingredient 86% | Example 7 Ratio of active ingredient 84% |
|---|---|---|---|---|---|---|---|---|
| Sitagliptin phosphate | | 248.12 g | 248.12 g | 248.12 g | 248.12 g | 248.12 g | 248.12 g | 248.12 g |
| Stearic acid (50) | | 40.0 g | 28.0 g | 20.0 g | 24.0 g | 32.0 g | 16.0 g | 24.0 g |
| Aminoalkyl methacrylate copolymer E | | 24.0 g | 16.0 g | 16.0 g | 16.0 g | 8.0 g | 24.0 g | 24.0 g |
| Production condition | Air supply temperature (°C) | 85-80 | 85-78 | 85-68 | 70-75 | 75-85 | 72-78 | |
| | Product temperature (°C) | 40-62 | 34-63 | 39-58 | 36-56 | 34-64 | 49-66 | |
| | Rotor rotation speed (rpm) | 400 | 400 | 400 | 400 | 400 | 400 | |
| | Melting time (min) | 22 | 29 | 45 | 25 | 45 | 60 | |
| Availability of production | | ○ | ○ | ○ | ○ | ○ | x | ○ |
| Particle size | $D_{10}$ (μm) | 126.2 | 145.1 | 44.2 | — | — | — | |
| | $D_{50}$ (μm) | 215.5 | 256.4 | 227.6 | — | — | — | |
| | $D_{90}$ (μm) | 329.6 | 412.1 | 363 | — | — | — | |
| Ratio of grain size distribution $((D_{90}-D_{10})/D_{50})$ | | 0.9 | 1 | 1.4 | 1 | — | — | — |

(—) is not measured.

Example 1

310.2 g of sitagliptin phosphate as an active ingredient, 37.5 g of stearic acid (NOF CORPORATION) as a melt component, and 37.5 g of aminoalkyl methacrylate copolymer E (Evonik, Eudragit (registered trademark) EPO) as a polymer were put into a tumbling granulator (Powrex Corporation, MP-01), and granulation was performed at a rotor rotation speed of 400 rpm, an air supply air volume of 0.24 L/min to 0.37 L/min, and a supply air temperature of 82.9 °C to 89.6 °C for 100 minutes. At this time, the temperature of the additive agents was 55.4 °C to 68.1 °C.

From the results of Examples 2 to 4, the granules of the present invention could contain the active ingredient in a very high ratio of 80 to 90% by mass with respect to the total mass of the granules. In addition, the particle size distribution of the granules of the Examples 2 to 4 was 0.9 to 1.4, indicating that the granules were uniform.

From the results of Examples 5 to 7 and Comparative Example 2, in the combination of stearic acid and Eudragit (registered trademark) EPO, under a formulation condition containing 86% by mass of the active ingredient which was a very high ratio based on the total mass of the granules, the mixing ratio of the melt component and the polymer is important, and if the polymer was contained in the mass ratio of the melt component to the polymer of 4:1 or more and less than 2:3, the production of the granules was possible.

According to one embodiment of the present invention, granules having a high content of an active ingredient and a uniform particle size are provided. Alternatively, according to one embodiment of the present invention, a preparation containing granules having a high content of an active ingredient and a uniform particle size is provided.

What is claimed is:

1. A granule comprising:

(a) an active ingredient, sitagliptin phosphate of the following formula:

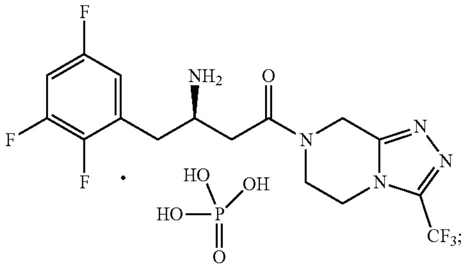

(b) a melt compound, stearic acid of the following formula:

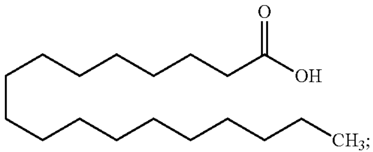

and (c) a polymer, aminoalkyl methacrylate copolymer E;

wherein the sitagliptin phosphate, the stearic acid, and the aminoalkyl methacrylate copolymer E are bound.

2. The granule according to claim 1, wherein the granule has a structure in which (a) the sitagliptin phosphate; (b) the stearic acid; and (c) the aminoalkyl methacrylate copolymer E are admixed with each other by melting.

3. The granule according to claim 1, wherein the granule has a structure in which a part of (a) the sitagliptin phosphate; (b) the stearic acid; and (c) the aminoalkyl methacrylate copolymer E are bound to each other by melting.

4. The granule according to claim 1, wherein the granule further comprises 50% or more of the sitagliptin phosphate by mass, with respect to the total mass of (a) the sitagliptin phosphate; (b) the stearic acid; and (c) the aminoalkyl methacrylate copolymer E.

5. A preparation comprising:

(a) the granule according to claim 1; and (b) at least one pharmaceutically acceptable additive agent.

6. The preparation according to claim 5, wherein at least one pharmaceutically acceptable additive agent is a disintegrant.

* * * * *